United States Patent
Backes et al.

(12) 
(10) Patent No.: US 6,401,769 B1
(45) Date of Patent: Jun. 11, 2002

(54) APPARATUS FOR DISPENSING A PREDETERMINED VOLUME OF A LIQUID

(75) Inventors: Monica Backes, Ealing; Anthony Robert Corless, Ash; John Edward Andrew Shaw, West Drayton; Alastair Sibbald, Maidenhead, all of (GB)

(73) Assignee: Central Research Laboratories Limited, Hayes (GB)

( * ) Notice: Subject to any disclaimer, the term of this patent is extended or adjusted under 35 U.S.C. 154(b) by 0 days.

(21) Appl. No.: 09/600,085

(22) PCT Filed: Jan. 18, 1999

(86) PCT No.: PCT/GB99/00163
§ 371 (c)(1),
(2), (4) Date: Dec. 18, 2000

(87) PCT Pub. No.: WO99/36176
PCT Pub. Date: Jul. 22, 1999

(51) Int. Cl.[7] ................................................. B65B 1/20
(52) U.S. Cl. .............................. 141/70; 141/31; 141/67; 141/62
(58) Field of Search ............................... 141/31, 67, 70, 141/62, 234, 237, 242, 243; 422/100, 101, 102

(56) References Cited

U.S. PATENT DOCUMENTS

| | | | |
|---|---|---|---|
| 3,765,461 A | * | 10/1973 | Keck |
| 4,052,320 A | * | 10/1977 | Jakubowicz |
| 4,271,119 A | * | 6/1981 | Columbus |
| 4,676,274 A | * | 6/1987 | Brown |
| 4,797,259 A | * | 1/1989 | Matkovich et al. |
| 5,599,502 A | * | 2/1997 | Miyazaki et al. |
| 6,083,761 A | * | 7/2000 | Kedar et al. |
| 6,103,199 A | * | 8/2000 | Bjornson et al. |

FOREIGN PATENT DOCUMENTS

| | | |
|---|---|---|
| DE | 196 48 458 C1 | 7/1998 |
| EP | 0 434 148 A3 | 6/1991 |
| JP | 56 133177 A | 10/1981 |
| JP | 08 252913 A | 10/1996 |
| WO | WO 97/01085 | 1/1997 |
| WO | WO 97/15394 | 5/1997 |
| WO | WO 00/67293 | * 11/2000 |

* cited by examiner

Primary Examiner—Gregory L. Huson
Assistant Examiner—Khoa Huynh
(74) Attorney, Agent, or Firm—William H. Bollman

(57) ABSTRACT

Apparatus for dispensing a predetermined volume of a liquid (18) comprises a reservoir (12) for the liquid, a channel (13) provided with an outlet (16) for conveying the liquid (18) from the reservoir to the outlet, and means for generating a pulse of gas. The apparatus is arranged such that the flow of gas causes a predetermined volume of liquid to be ejected from the outlet. The outlet comprises a pair of openings in the channel which face one another, the liquid being retained between the openings by surface tension in the absence of a flow of gas. The gas flow is directed towards one of said openings in use. The apparatus may be used to dispense volumes of a liquid reagent in the range 1 nl to 2 μl. The apparatus avoids contamination of the liquid, and dispensing head construction allows devices to be low cost disposable units. The apparatus is less sensitive to liquid viscosity than existing devices.

18 Claims, 4 Drawing Sheets

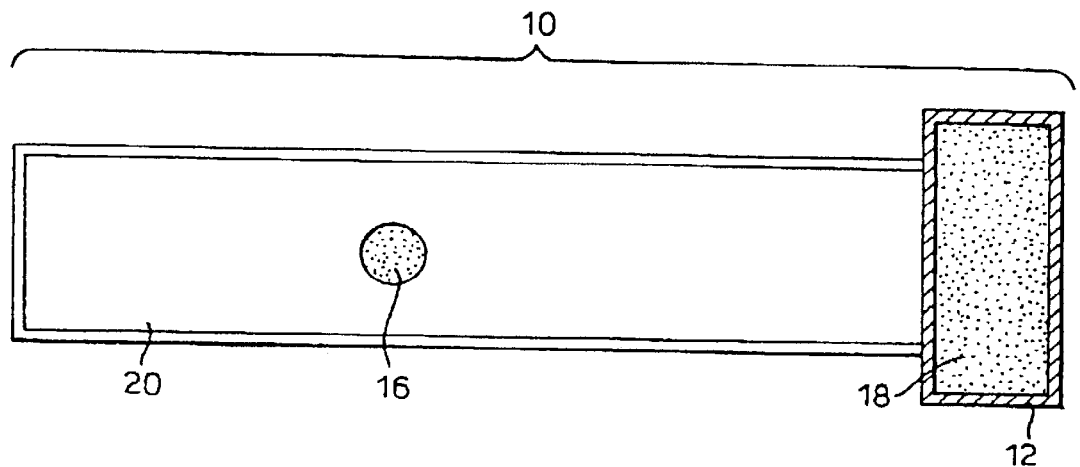
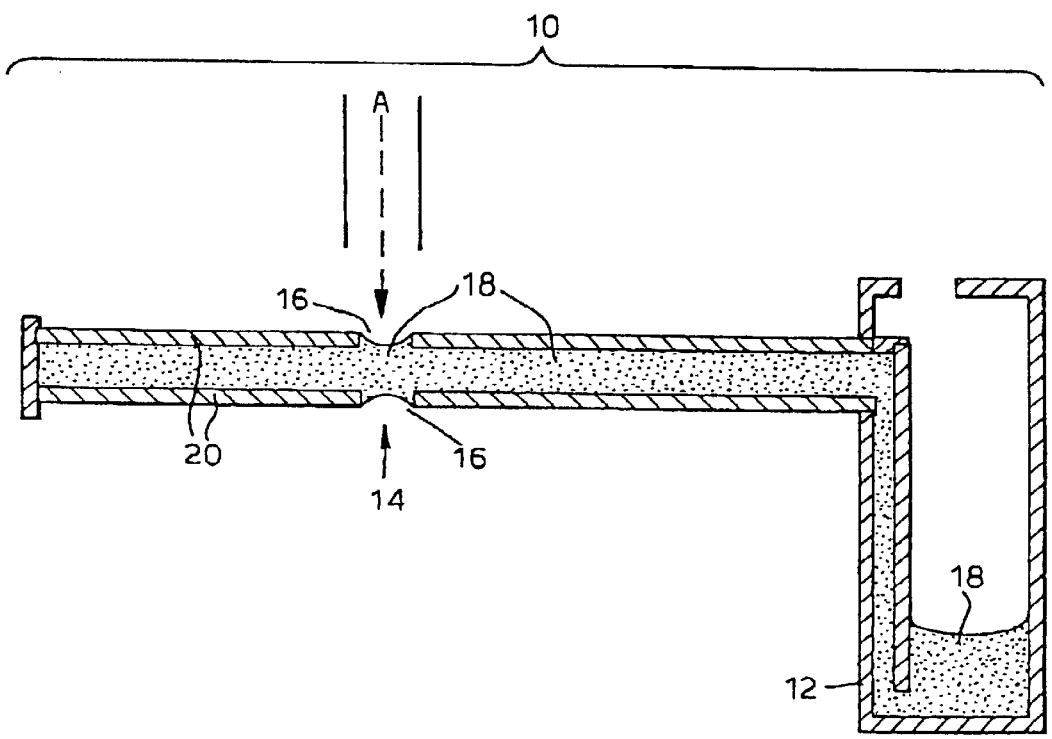

APPARATUS FOR DISPENSING A PREDETERMINED VOLUME OF A LIQUID

This invention relates to apparatus for dispensing a predetermined volume of a liquid, comprising a source or reservoir for the liquid, a channel provided with an outlet for conveying the liquid from the source or reservoir to the outlet, and means for generating pulse of gas, the apparatus being constructed and arranged such that in use said pulse of gas causes a predetermined volume of liquid to be ejected from said outlet. It relates particularly, though not exclusively, to apparatus for dispensing biochemical reagents. Dispensers for dispensing biochemical reagents can provide a non-contact means for dispensing small volumes of a liquid, commonly in the range 0.1 nl to 100 $\mu$l. Dispensers based on conventional ink jet printer technologies are most generally applied for dispensing volumes in the 0.5 nl to 10 nl range.

Accurate and rapid dispensing of reagents is very important in high-throughput applications. Dispensers which may be used for automated dispensing of reagents and solutions for synthesis, including combinatorial chemistry, and for chemical and biochemical testing are hereinafter referred to as reagent dispensers.

A reagent dispenser is described in an article entitled "Characterisation of an ink-jet chemical micro dispenser for combinatorial library synthesis", which was published in Analytical Chemistry, Vol. 69, No. 4, February 1997, at page 543. The dispenser is complex and requires three different types of solenoid valves to control the delivery of a pressurised gas which dispenses reagent.

Another device is described in published International Patent Application WO 9715394. This device consists of a multi-well plate where the wells have a large opening at the top and a small opening in the base through which a liquid is ejected when a pressure pulse is applied to the top surface of the liquid.

According to a first aspect of the present invention there is provided apparatus as defined in claims 1–10. According to a second aspect of the invention there is provided a liquid handling system as defined in claims 11–15.

Known dispensers have difficulty in dispensing sufficiently small volumes of liquid to meet current and future requirements. Moreover, the liquids which must be dispensed in biochemical applications can vary considerably in viscosity and may be sensitive to heat, pressure and/or liquid shear forces, this renders the use of conventional ink-jet dispensing techniques extremely difficult.

Cross contamination of dispensing mechanisms by different reagent liquids is another problem in the use of dispensers in chemical and biological synthesis and testing. It is desirable that liquid handling components should be cheap and therefore disposable to reduce the need for expensive and possibly unreliable washing procedures. Known ink-jet mechanism based systems involve relatively complex components contacting the dispensed liquid, and are generally too expensive to be treated as disposable components.

The present invention can provide a simple structure for rapidly delivering liquid to one or more collecting sites where reproducible liquid droplets may be repeatedly generated without contact to the collecting sites, and where the droplet ejecting force is provided by a separate air or gas stream control. This allows the actuating element to be confined to the air or gas stream, avoiding contact with the dispensed liquid and possible contamination. The simple structure enables manufacture at low cost.

The performance of conventional ink-jet printer mechanisms, in which the droplet actuating mechanism contacts or is immersed in the liquid to be dispersed, is grossly affected by the viscosity of that liquid. The present invention provides a means whereby the actuating mechanism is not directly in contact or affected by the liquid, and can be widely adjusted to cope with various liquid viscosities. The simple geometry whereby a slug of liquid is confined between orifices in thin planar sheets will result in ejection forces which are not strongly dependant on liquid viscosity.

A common cause of failure in reagent dispenser delivery systems is spattering of chemical solvents from the base of shallow wells (typically arranged in an array on a tray) into which reagent is dispensed. The result is that liquid spills into adjacent wells. This has limited the performance of known dispensers.

The invention provides apparatus which can be constructed to dispense liquid volumes selected in the range, for example, of 1 nl to 1 $\mu$l for the range of solution and liquid viscosity commonly encountered in biochemistry, with good volumetric control and adequate repetition rate.

The invention will now be described in more detail, by way of example only, with reference to the accompanying drawings, in which:

FIG. 3 illustrates a plan view of a dispenser connected to a reservoir.

FIG. 4 illustrates a cross-sectional view of a dispenser connected to a reservoir where capillary action along supplies dispensing liquid to the dispenser head.

Figure 5:
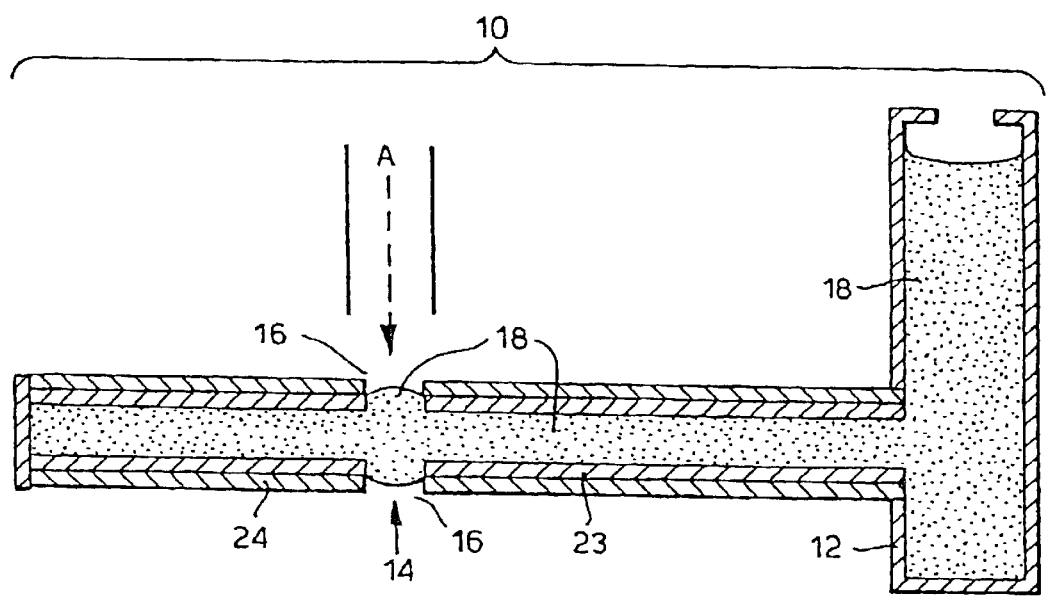
FIG. 5 illustrates a cross sectional view of a dispenser connected to a reservoir where hydrostatic pressure supplies dispensing liquid to the dispensing head.
Figure 6:
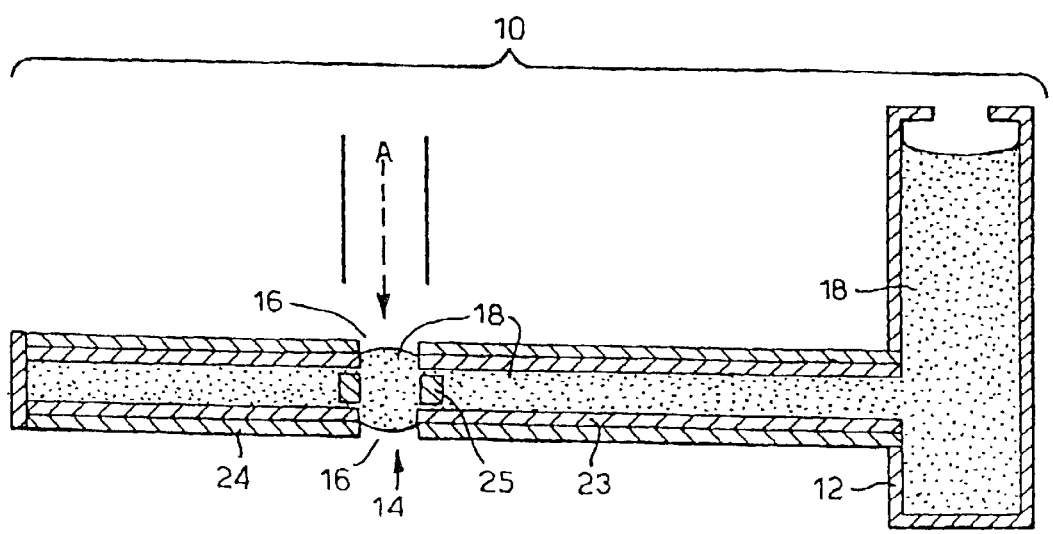
FIG. 6 illustrates a cross sectional view of a dispenser as in FIG. 5 but where a partial barrier to flow is provided within the channel around an outlet.

Referring to the Figures, a dispenser 10 comprises at least one reservoir 12. Connected to the reservoir 12 is a liquid pathway or channel 13 which leads to a dispensing head 14. In the dispensing head 14 there is provided an outlet, in the present example defined by at least one pair of orifices or openings 16. Orifice pairs 16 allow selective dispensing of reagent 18. Delivery of reagent 18 to the orifice pairs 16 is by means of flow along pathway 13, which may be driven by hydrodynamic and/or capillary forces. Orifices are defined in adjacent planar sheets 20a and 20b which define the dispensing head 14. The liquid is confined between orifices 16 forming pairs in the dispensing head 14 by capillary force (i.e. surface tension). The conditions for filling the space between the orifices 16 and confirming liquid there until ejected by a gas pressure pulse are set by controlling channel and orifice dimensions, hydrostatic pressures, and the wettability of material used to construct the dispenser. Where reservoir filling height generates hydrodynamic pressure tending to drive liquid out of the orifices 16, as shown in FIGS. 1, 2, 5 and 6, it is necessary to choose material for the outer surfaces of the sheets 20a and 20b in FIG. 1 such that it is not preferentially wetted by the liquid. Sheets forming the dispenser may be formed as laminates or coated to provide different wetting properties. In FIGS. 5 and 6 the internal surfaces 23 may be preferentially wetted by the liquid, whilst the external surfaces 24 are preferentially not wetted by the liquid. Hydrodynamic pressures in the liquid to fill the structure defined by the sheets is set below the bubble pressure for the orifices 16. Reagent 18 can be ejected through one of the orifices 16 by a pulse of gas supplied by a pressure source (not shown), in the direction of arrow A, substantially orthogonal to the plane of the orifice 16 and thus orthogonal to the reagent feed direction. The direction of arrow A also defines for this embodiment an axis common to the pairs of openings 16. Reagent 18 may be dispensed into a plurality of wells 21 which may be in the form of a microtitre plate 22. Wells in plate 22 have a micro-textured finish applied to their inner surfaces to reduce splashing. The spacing between adjacent wells in plate 22 is the same as the spacing, between adjacent dispensing head 14. Dispensed reagent 18 is replenished by flow driven by hydrodynamic and capillary forces acting over the local area of the sheets 20 so as to drive liquid towards orifices 16.

The volume of reagent 18 held ready for ejection from the dispenser head 14 is determined by the area of overlap of the orifices that form a pair, and by their separation in the direction of ejection. The volume of reagent 18 in the immediate path of the gas pulse is dispensed. Provided the duration of the gas pulse is short compared with the time taken for the space between the two orifices to be filled, the volume of reagent dispensed by each gas pulse is well defined and reproducible. Dispensing of reagent 18 into wells 21 of a micro-well plate 22 (shown in detail in FIG. 2) is achieved by simultaneously controlling gas pulse production, and the positioning and displacement of the micro-well plate with respect to the dispenser 10.

Provided that liquid adjacent the orifice is not entrained in the gas flow, then the dispensing action is essentially to eject a defined, approximately cylindrical volume from the liquid. The condition that volume of reagent 18 dispensed in each pulse is well defined and reproducible may be achieved by firstly maintaining the gas pulse duration to be short compared to the time to refill the orifice pair 16 as mentioned above, the secondly by providing a solid structure partially obstructing liquid flow into the opening defined by the orifice pair. This is illustrated in FIG. 6 where this solid structure 25 may be a separate component, porous body, or formed from the plane materials in which the orifices are defined. Such solid structures 25 will generally only be required for dispensers formed to yield droplets greater than 10 nl.

Figure 1:
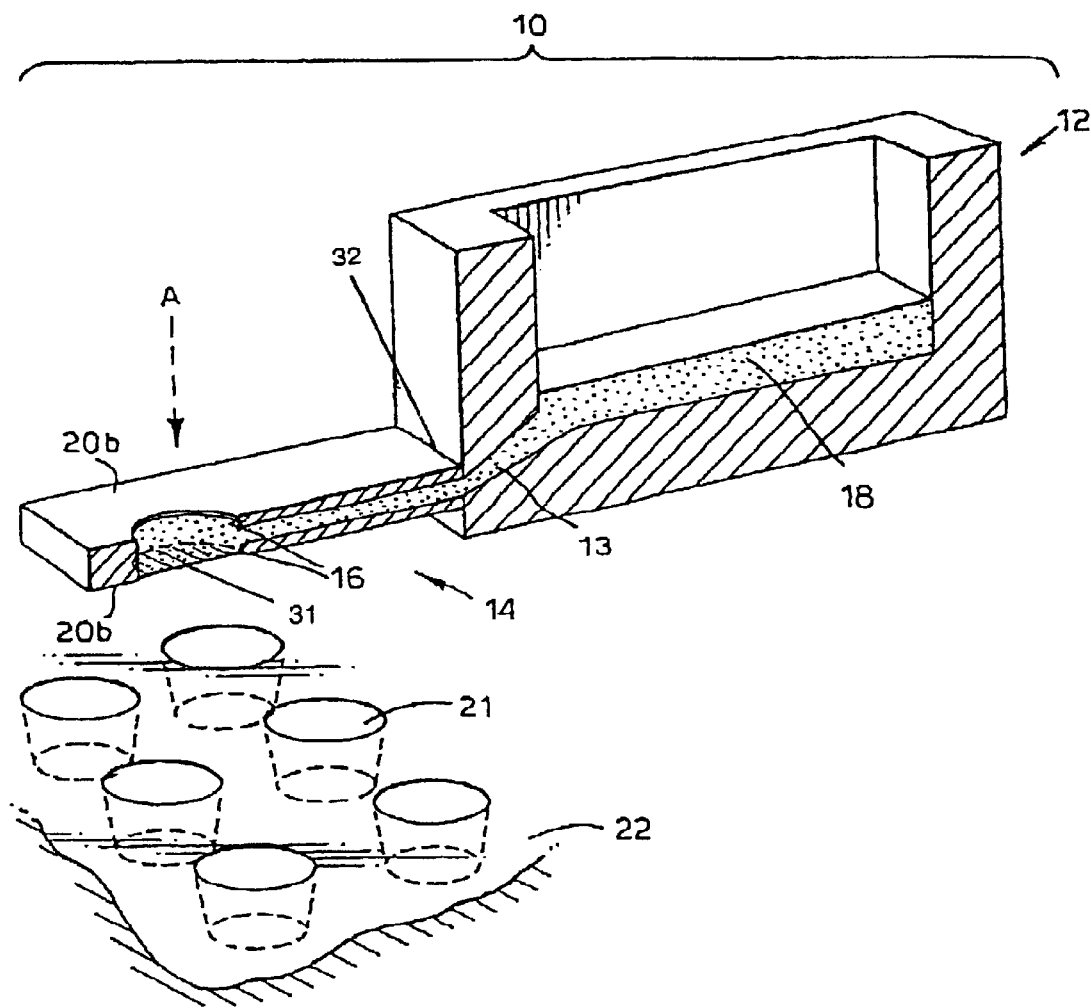
FIG. 1 illustrates a three dimensional, part-sectional view of a dispenser showing a dispensing head and a reservoir.
Figure 2:
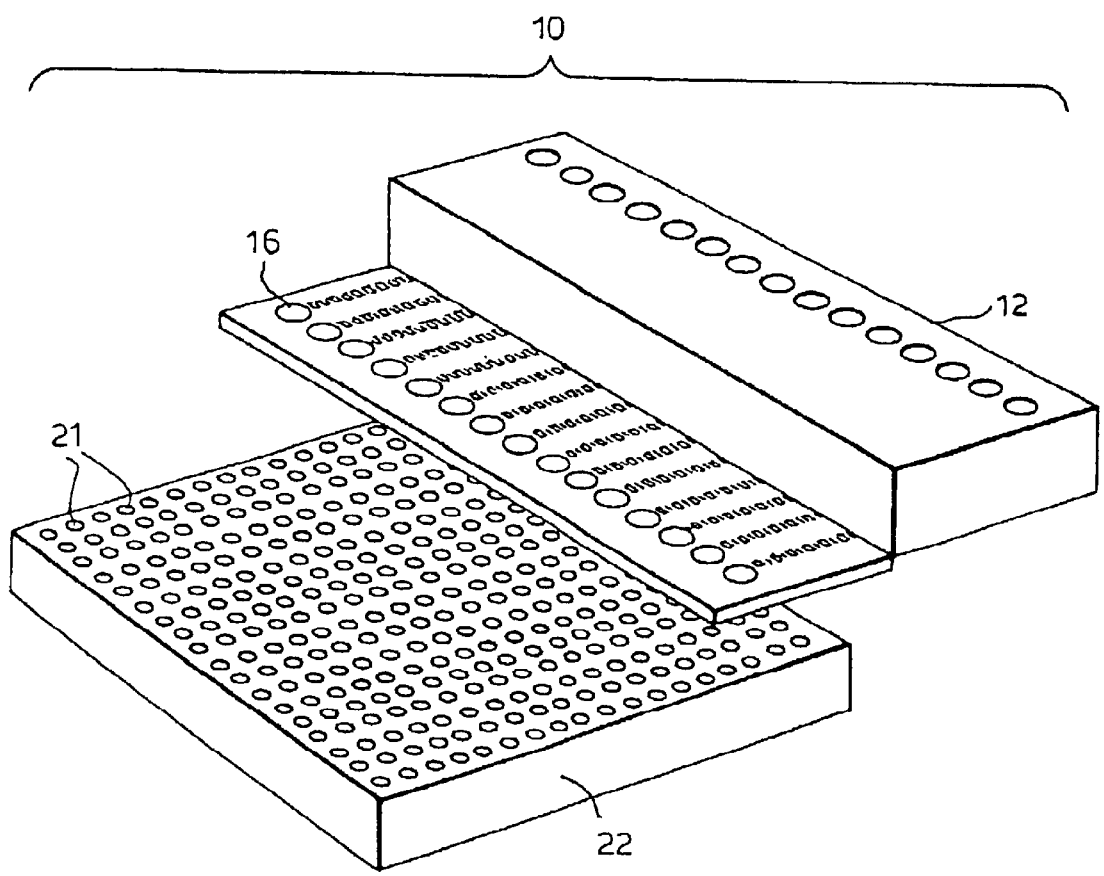
FIG. 2 illustrates an overall diagrammatic view of a multi-dispenser together with a tray of wells.

Orifice 16 shown in FIG. 1, may be replaced with a fine mesh or grill 31. The mesh or grill allows liquids of low surface energy to be supported until an ejecting gas pulse is applied. This aspect of the invention thus enables liquids having low surface energies to be dispensed.

In the present invention the combination of capillary action, gravitation and external pressure feeds liquid from the reservoir to the orifice pairs. A means of applying a short time acting force essentially orthogonal to the plane defining the orifice pairs (essentially along the common axis of the orifice pairs) overcomes the surface tension and ejects an aliquot of liquid. The volume of this aliquot is determined essentially by the planar dimensions of the orifices, the spacing between the orifices along their common axis, and the surface tension defining the meniscus of the liquid.

Dispensers according to the present invention may be constructed by forming a channel or conduit with one or more overlapping orifice pairs formed across the conduit providing liquid ejection sites and facing one another. The conduit may be formed between plane sheet materials with the space between the sheets set sufficient to allow flow of the liquid to be dispensed between the sheets and one or more overlapping orifice pairs formed through the sheets arranged to provide liquid ejection sites. The orifices may be formed in individual sheets which are then aligned, or may be formed through the sheets after construction of a conduit. The space between the sheets may contain spacer elements, liquid guides, and porous materials.

It will be appreciated that alternate structures are possible which do not depart from the physical principles underlying the operation of the device. For example, the conduit or channel may be formed in a capillary tube, such as a circular capillary, with the orifices therein being drilled through the tube walls, or otherwise introduced by mechanical, chemical, optical or other machining means. In such a case there will be variations in the disposed volume compared to the case of a simple coplanar geometry the effect of which may be derived by geometric calculations pertaining to the particular dimensions.

The supply of dispensing liquid through the dispenser to orifice pairs and filling of the space between orifices which form a pair may be driven by capillary action alone or by hydrostatic pressure or by a combination of capillary and hydrostatic forces. Hydrostatic forces may be generated by a raised liquid reservoir or other system applying force to the liquid such as a pump or connection to an elevated gas pressure reservoir. Liquid is retained between orifices which form a pair by capillary forces until these are overcome by an ejection impulse provided by a gas pressure pulse applied on one side of an orifice pair.

Where the liquid reservoir is connected to the dispensing head so that hydrostatic pressure would not push liquid through to orifice pairs, as where the level of liquid in the reservoir is below orifice pairs, then capillary action is required to draw liquid through the dispenser into the space between orifices which form pairs. Parts at least of the surfaces inside the conduit to orifice pairs and the internal surfaces of the orifices are formed of material preferentially wetted by the dispensing liquid. Preferentially wetted means that the contact angle within a drop of liquid on a material is less than 90 degrees. The upper limits on orifice dimensions and vertical distance for capillary feed from liquid surface in a reservoir consistent with capillary feed may be readily obtained from liquid density, surface tension, contact angles and dimensions using the expressions for capillary constant or rise which may be found in many standard texts.

Where sufficient hydrostatic pressure is provided to drive liquid through the dispensing head to fill the space between orifices which form pairs, it is necessary to provide material not preferentially wetted by the dispensing liquid at least on the external surfaces around the orifices. Where dispensers are formed from sheet materials, and depending on dimensions and the presence of easily wetted materials between the sheets, the sheets may be formed partly or entirely of materials not preferentially wetted by the dispensing liquids. By not preferentially wetted it will be understood that the contact angle made between a drop of the liquid and the surface of the material is greater than 90 degrees. Where the dispensing liquids are aqueous solutions it is preferred to use low energy surface materials such as PTFE or similar compounds for the sheet materials or for external coatings on the sheet materials at least around the orifice pairs. The limits on orifice dimensions and hydrostatic pressure consistent with retention by capillary forces of liquid between the orifices which form a pair may be readily obtained from hydrostatic pressure, surface tension, contact angles and dimensions using the expressions for bubble pressure which may be found in many standard texts.

Although for the case where capillary action alone drives liquid into the dispenser and the space between orifice pairs it is not necessary to have external surfaces adjacent to the orifices which are not preferentially wetted by the dispensing liquid, it is an advantage to do so as the possibility of liquid wicking across surfaces between orifices is mitigated.

Dispenser elements according to the present invention may be constructed to be demountably linked 32 to liquid reservoirs or other liquid supply, and may be separately cleanable or disposable.

Dispenser elements according to the present invention may be constructed to be demountably linked to the gas pulse generation equipment.

A dispenser formed in accordance with the invention has a number of advantages over prior art devices. By changing the size of the aperture of the orifice and/or by varying the gap between the capillary filled orifice (or orifices), and/or receptacles (or wells) into which reagent is dispensed, the volume of reagent ejected can be varied. By using a very fine mesh to support liquids with low surface energy, a wider range of reagents may be dispensed. The volume of reagent to be dispensed is preferably 1 nl or greater, and preferably the volume is less than 2 $\mu$l.

The dimensions of orifices and distance through the dispenser between overlapping orifice pairs defines approximately the liquid delivery volume. Upper limits on the orifice dimensions are set by the requirement that surface tension effects must retain liquid between the orifice parts until ejected by an impulse supplied by air or gas jet. In practice this limits diameter of each orifice to 1 mm or less. Orifice shape will most generally be circular but other shapes may be used such as elliptical, square, rectangular, hexagonal and triangular. The overlapping orifices which form a pair may have substantially the same dimensions but it is acceptable for their dimensions to differ as long as capillary action retains liquid between the orifices. Where the dimensions of orifices which form a pair differ, the dispensed volume will be primarily controlled by the smaller orifice as long as the gas impulse is sufficiently short. Example dimensions which may be used where each orifice is circular and the approximate volumes defined for delivery between orifice pairs are shown in Table 1:

TABLE 1

| Orifice Diameter mm | Orifice Separation mm | Approximate Volume nl |
|---|---|---|
| 1 | 1 | 750 |
| 0.2 | 0.5 | 75 |
| 0.1 | 0.1 | 7.5 |
| 0.05 | 0.05 | 2 |
| 0.05 | 0.03 | 1 |

The wells into which the reagent is dispensed preferably have micro-textured inner surfaces to overcome the problem of reagent splashing, thus allowing liquid droplets to be broken up and scattered sideways within the well.

One reservoir may supply a plurality of orifice pairs with liquid. Each pair of such a plurality may be subjected to ejection gas pulses at the same time, or at different times, i.e. sequentially.

An orifice pair may be connected to one or more reservoirs, especially where multiple reservoirs containing the same reagent are employed to aid continuous use. Multiple reservoirs containing different liquids may be used where it is desirable that the corresponding liquids come into contact, or are mixed, before or during dispensing. It may be arranged that the channels from different reservoirs become joined only adjacent the orifices.

Apparatus in accordance with this invention may be oriented to eject liquid in any direction. Receptacles to receive the ejected liquid may be formed of or comprise material to absorb or otherwise retain the liquid.

What is claimed is:

1. An apparatus for dispensing a predetermined volume of a liquid, comprising:

at least one of a source and a reservoir for said liquid;

a channel for conveying liquid from at least one of said source or said reservoir, said channel being defined by a pair of substrates having spacer elements between them and having internal surfaces and external surfaces, said channel also being provided with an outlet; and means for generating a pulse of gas;

wherein said apparatus is constructed and arranged such that in use said pulse of gas causes a predetermined volume of said liquid to be ejected from said outlet, characterized in that said outlet comprises a pair of openings in said channel which face one another, said liquid being retained between said pair of openings in an absence of said pulse of gas by surface tension at each of said openings, said pulse of gas being directed towards one of said pair of openings to at least one of dispense and eject said predetermined volume of liquid from the other opening of said pair of openings, wherein said predetermined volume of liquid dispensed or ejected is determined essentially by planar dimensions of said pair of openings and spacing between said pair openings along an axis common to said pair of openings.

2. The apparatus according to claim 1, wherein:

a direction of said pulse of gas is substantially orthogonal to a direction of liquid flow along said channel from said reservoir.

3. The apparatus according to claim 1, wherein:

at least one of said pair of openings is provided with a porous membrane or mesh.

4. The apparatus according to claim 1, wherein:

said reservoir and said channel are releasably secured to said means for generating a pulse of gas.

5. The apparatus according to claim 1, further comprising:

a plurality of channels provided with a plurality of outlets, each of said plurality of outlets comprising a pair of openings which face one another.

6. The apparatus according to claim 1, wherein:

said channel comprises a capillary tube, and said pair of openings are formed therein by at least one of drilling, mechanical, chemical, optical and other machining techniques.

7. The apparatus according to claim 1, wherein:

said channel is releasably secured to at least one of said source and reservoir.

8. The apparatus according to claim 1, wherein:

said internal surfaces of said channel comprise material which is preferentially wetted by said liquid to be at least one of dispensed and ejected, and where said liquid is fed to said outlet by capillary action.

9. The apparatus according to claim 1, wherein:

said external surfaces of said channel, at least in regions through which said openings are formed, comprise materials not preferentially wetted by said liquid to be at least one of dispensed and ejected, said liquid being urged along said channel by at least one of hydrodynamic and capillary forces.

10. The apparatus according to claim 1, further comprising:

a receptacle for receiving liquid at least one of dispensed and ejected from said apparatus.

11. The apparatus according to claim 10, wherein:

said receptacle has surfaces adapted to prevent splashing of said liquid.

12. The apparatus according to claim 10, wherein:

said receptacle comprises a medium which at least one of absorbs and retains said liquid.

13. The Apparatus according to claim 10, wherein:

said receptacle comprises a substrate having at least one of a plurality of wells and liquid collection sites for at least one of receiving said dispensed liquid or ejected liquid.

14. The apparatus according to claim 13, wherein:

said apparatus includes a plurality of outlets, each of said plurality of outlets being registrable with at least one of said plurality of wells and liquid collection sites.

15. The apparatus according to claim 13, wherein:

said receptacle comprises a microtitre plate.

16. The apparatus according to claim 1, wherein:

said volume of said liquid is between 1 nanoliter and 1 microliter.

17. The apparatus according to claim 1, wherein:

each opening of said pair of openings has substantially the same dimensions.

18. The apparatus according to claim 1, further comprising:

a structure partially obstructing flow of said liquid in said channel into said outlet is defined by said pair of openings.

* * * * *